United States Patent

Rogiers et al.

Patent Number: 5,885,931
Date of Patent: Mar. 23, 1999

[54] COMPOSITION COMPRISING LIQUID FERTILIZER, TOXICANT AND COMPATIBILITY AGENT

[75] Inventors: Lodewijk M Rogiers, Haacht; Jean-Pierre Stoefs, Brussels, both of Belgium

[73] Assignee: Imperial Chemical Industries PLC, London, England

[21] Appl. No.: 626,950

[22] Filed: Apr. 3, 1996

Related U.S. Application Data

[62] Division of Ser. No. 186,897, Jan. 27, 1994, abandoned, which is a continuation of Ser. No. 924,609, Jul. 27, 1992, abandoned, which is a continuation of Ser. No. 602,397, Oct. 24, 1990, abandoned, which is a continuation of Ser. No. 218,999, Jul. 14, 1988, abandoned.

[30] Foreign Application Priority Data

Jul. 17, 1987 [GB] United Kingdom ............... 8716949

[51] Int. Cl.$^6$ ............... A01N 25/30; B01F 17/16; B01F 17/56; C05G 3/06
[52] U.S. Cl. ............... 504/101; 71/DIG. 1; 252/312; 252/357; 504/116
[58] Field of Search ............... 252/312, 357, 252/DIG. 1; 71/DIG. 1; 504/101, 116

[56] References Cited

U.S. PATENT DOCUMENTS

| | | | |
|---|---|---|---|
| 4,224,049 | 9/1980 | Devisetty et al. | 71/97 |
| 4,240,921 | 12/1980 | Kaniecki | 252/DIG. 1 |
| 4,313,847 | 2/1982 | Chasin et al. | 252/356 |
| 4,488,981 | 12/1984 | Urfer et al. | 252/DIG. 1 |

FOREIGN PATENT DOCUMENTS

| | | |
|---|---|---|
| 0006348 | of 0000 | European Pat. Off. . |
| 0070074 | 1/1983 | European Pat. Off. . |
| 0075995 | 4/1983 | European Pat. Off. . |
| 0190995 | 1/1986 | European Pat. Off. . |
| 0075996 | 1/1987 | European Pat. Off. . |
| 0092877 | 7/1987 | European Pat. Off. . |

OTHER PUBLICATIONS

The Condensed Chemical Dictionary, Sixth Edition, Edited by Arthur & Elizabeth Rose, Reinhold Publishing Corp., New York (1961), p. 544 [QD5C5 1961 C38].

*Primary Examiner*—Richard D. Lovering
*Attorney, Agent, or Firm*—Pillsbury Madison & Sutro LLP

[57] ABSTRACT

A composition which contains a glycoside, an ethoxylated alkylamine, a polyoxyalkylene alkylphenol phosphoric acid ester, a glycol and optionally water can be used as a compatibility agent for a liquid fertiliser-toxicant mixture. The composition has a high flash point, is liquid at temperatures below 0° C. and its properties do not change after being stored for one week at 40° C. The composition provides improved compatibility for a wide range of liquid fertiliser-toxicant mixtures and for mixtures of different toxicants when used in different pesticide formulations.

3 Claims, No Drawings

COMPOSITION COMPRISING LIQUID FERTILIZER, TOXICANT AND COMPATIBILITY AGENT

This is a division of application Ser. No. 08/186,897, filed Jan. 27, 1994, now abandoned, which is a continuation of application Ser. No. 07/924,609, filed on Jul. 27, 1992, now abandoned, which is a continuation of application Ser. No. 07/602,397, filed Oct. 24, 1990, now abandoned, which is a continuation of application Ser. No. 07/218,999, filed Jul. 14, 1988, now abandoned.

The present invention relates to compositions which are suitable for use as compatibility agents, especially for liquid fertiliser-toxicant mixtures or for mixtures of toxicants when these are used in different pesticide formulations.

Present day farming is, in many countries, very intensive and removes nutrients from the soil. The soil is replenished with fertilisers and for convenience liquid fertilisers are used which are capable of being sprayed onto the soil. To save time and money, it is desirable to effect the spraying of fertilisers and toxicants as a single operation using a mixture of fertiliser and toxicant. The term "toxicant" is used herein to include any active ingredient which is used, either alone or as a mixture with other components, to control the occurence of unwanted species, such as weeds, insect pests or fungi, and hence includes, but is not restricted to, the active ingredient of herbicides, insecticides and fungicides. The toxicant is conveniently used by being applied to the soil, particularly by spraying. Many toxicants are used in admixture with other components such as fillers, solvents or suspending agents, surfactants and the like and such admixtures will be referred to hereafter as "pesticides". In addition to saving time and money by effecting a single spraying operation using a fertiliser-toxicant and/or fertiliser/pesticide mixture, such a procedure may also achieve a further advantage in reducing soil compaction.

However, it has been found that many mixtures of fertiliser and toxicant and/or pesticide are incompatible or form unstable mixtures which soon separate. The use of an incompatible or separated mixture generally makes it impossible for the farmer to achieve an even distribution of the products over the soil and this results in inefficient use of expensive materials and can lead to crop injury and hence a poor crop yield. Accordingly, it is desirable to add to the mixture of fertiliser and toxicant and/or pesticide a material which improves the compatibility of the fertiliser and the toxicant and/or pesticide.

In EP-A-0006348 there is disclosed an emulsifier/surfactant composition which can be used to form pesticide formulations, including with fertilisers. The composition of EP-A-0006348 comprises a polyoxyalkylene alkyl or alkylaryl ether phosphate ester, a polyoxyalkylene alkylamine, and a material selected from the group consisting of nonionic polyoxyalkylated surfactants, polyhydric alcohol esters and polyoxyalkylene glycols.

In U.S. Pat. No. 4224049 there is disclosed a compatibility agent which is an aqueous-lower alkanol solution containing an alkaryl polyoxyethylene glycol phosphate ester. The preferred compatibility agent is indicated to be 20% methanol, 16% water and 64% octylphenol polyoxyethylene glycol phosphate ester. A composition of this general type is commercially available as a compatibility agent.

A further commercially available compatibility agent is a mixture of 70% w/w of aqueous sorbitol containing 70% w/w of sorbitol; 15% w/w of an aqueous solution containing 45% w/w of sodium dodecyldiphenyloxide disulphonate; and 15% w/w of an aqueous solution containing 35% w/w of tetrasodium-N-(1,2-dicarboxyethyl)-N-octadecylsulphosuccinamate.

We have now obtained a compatibility agent which is as effective as, and is generally more effective than, the commercially available compatibility agents.

According to the present invention there is provided a composition which comprises (A) a glycoside;
(B) an alkoxylated alkylamine;
(C) a polyoxyalkylene alkyl or alkylaryl ether phosphoric acid ester; and
(D) a glycol.

As will be explained in more detail hereafter, components (B) and (C) may include a polyglycol such as polyoxyethylene glycol, which polyglycols result from the preparation of (B) and (C). Hereafter, references to (B) and (C) include the presence of any polyglycols which are also present with the amine or ester.

The composition may also contain water. Additionally, if desired, the composition may contain other ingredients which do not adversely affect the properties of the composition such as, for example, colouring agents such as water soluble dyes; defoaming agents such as water soluble and water insoluble surfactants and silicones; spreader/stickers such as silicone surfactants; and spray oils.

The proportion of components (A), (B), (C) and (D) which are present in the composition can be varied over a wide range. However, it is generally preferred that components (A) and (B) are each present in an amount of at least 5% by weight, particularly at least 10% by weight, relative to the weight of the total composition. The total composition as used herein refers to the total weights of (A), (B), (C) and (D). It is especially preferred that components (A) and (B) are each present in an amount of at least 20% by weight. The amount of each of components (A) and (B) preferably does not exceed 50% by weight and especially is not more than 40% by weight. Component (C) is preferably present in an amount of at least 5% by weight, particularly at least 10% by weight and especially at least 15% by weight. The amount of component (C) preferably does not exceed 40% by weight and especially is not more than 30% by weight. Component (D) is present in an amount of at least 2% by weight, particularly at least 5% by weight. The amount of component (D) preferably does not exceed 25% by weight and especially is not more than 20% by weight. It will be appreciated that in all compositions in accordance with the present invention, the amounts of components (A), (B), (C) and (D) aggregate to 100% by weight. A particularly preferred composition in accordance with the present invention contains 15 to 35% by weight of (A), 15 to 40% by weight of (B), 15 to 28% by weight of (C) and 5 to 25% by weight of (D).

If the composition additionally includes water, the proportion of water typically does not exceed 40% by weight of (A), (B), (C), (D) and water. Typically the amount of water is not less than the amount of component (D). Conveniently, if water is present in the composition, the amount of water (by weight) is greater than the amount of component (D) (by weight).

Component (A) of the composition is a glycoside and may be a monoglycoside, a polyglycoside or a mixture thereof. The glycoside is typically a compound which can be represented by the general formula:

$$R(OG)_a$$

where:
R is a hydrophobic moiety;
G is a saccharide group; and
a has a value of at least one.

The group R can be a hydrocarbyl group, a substituted hydrocarbyl group, a hydrocarbonoxy group or a substituted hydrocarbonoxy group. The group R can be an alkyl, cycloalkyl, aryl, alkaryl, aralkyl, alkenyl, alkoxy or aryloxy group and is preferably an alkyl or alkoxy group. The group R conveniently contains from 4 to 30 carbon atoms, preferably from 6 to 24 carbon atoms and especially from 8 to 18 carbon atoms. The group R can be a mixture of different groups, for example a mixture of alkyl or alkoxy groups containing different numbers of carbon atoms. Thus, R can be a mixture of alkyl or alkoxy groups which contain, on average, 9, 10 or 11 carbon atoms, particularly a mixture of alkyl or alkoxy groups containing from 8 to 10 carbon atoms and averaging 9 carbon atoms.

The saccharide group G may be derived from fructose, glucose, mannose, galactose, telose, gulose, allose, altrose, idose, arabinose, xylose, lyxose and ribose or from mixtures thereof. The group G is conveniently derived from glucose units and the glycoside is then a glucoside.

The value of a is the degree of polymerisation. When a is one the glycoside is a monoglycoside. Typically the value of a is greater than one and the glycoside is a mixture of polyglycosides, a mixture of a monoglycoside and a polyglycoside, or a mixture of a monoglycoside with a mixture of polyglycosides. The average value of a is typically at least 1.1, particularly at least 1.2 and especially at least 1.3. The average value of a is typically not greater than 8, particularly not greater than 4 and especially not greater than 2.

When the glycoside is an alkyl glucoside, the average value of a is conveniently between 1 and 2, for example about 1.5. We have obtained useful results when the glycoside is an alkyl glucoside of the general formula:

$$C_nH_{(2n+1)}O(C_6H_{10}O_5)_bH$$

where:
n has an average value of 9; and
b has a value of greater than one and not more than two.

Hydrocarbyl glycosides are commercially available materials for example as APG 225 Glycoside or as Triton BG 10.

Component (B) of the composition is an alkoxylated alkylamine. This component typically has the formula:

$$R^1R^2R^3_N$$

where:
$R^1$ is a hydrocarbyl group;
$R^2$ is a hydrocarbyl group or a group $(AO)_mH$;
$R^3$ is a group $(AO)_pH$;
A is an alkylene group;
m is zero or has a value of at least one and not more than 100;
p is zero or has a value of at least one and not more than 100;
and
(m+p) has a value of at least one and not more than 100.

The group $R^1$ is typically an alkyl group, for example an alkyl group containing up to 36 carbon atoms. It is preferred that $R^1$ is a higher alkyl group, that is one containing at least 6 carbon atoms. The group $R^1$ very preferably contains from 9 to 24 carbon atoms. The group $R^1$ may be a mixture of groups and preferably such a mixture contains, on average, from 9 to 24 carbon atoms.

Component (B) is conveniently prepared by reacting an alkylene oxide or a mixture of alkylene oxides, preferably ethylene and/or propylene oxide, with an alkylamine. The alkylamine reacted with the alkylene oxides, or alkylene oxide mixture, is preferably a primary amine in which the nitrogen atom is attached to a terminal carbon atom of the alkyl group. The amine can be derived from naturally occurring products such as tallow, coconut, soybean, or cotton seed oils and such an amine is a mixture of amines in which the hydrocarbyl groups ($R^1$) are alkyl groups containing from 12 to 18 carbon atoms. Synthetic alkylamines in which the hydrocarbyl groups ($R^1$) are alkyl groups containing from 12 to 18 carbon atoms may also be utilised. We have obtained a useful result when the group $R^1$ is a mixture of alkyl groups containing 13 to 15 carbon atoms The group $R^2$ can be a hydrocarbyl group which is as described for the group $R^1$. However, $R^2$ is typically a group $(AO)_mH$.

The alkylene group A typically contains from 2 to 5 carbon atoms, for example as in an ethylene, propylene or butylene group, and is especially an ethylene group.

As previously described herein, component (B) is conveniently prepared by reacting an alkylene oxide or mixture of alkylene oxides such as ethylene, propylene and/or butylene oxide, with an alkylamine. During such a preparation, alkylene oxide chains are formed on the nitrogen atom of the amine but some of the alkylene oxide may not condense with the amine but undergoes polymerisation separately from the amine to form a polyoxyalkylene glycol. Separation of the polyoxyalkylene glycol from the alkoxylated alkylamine is not commercially viable and hence the alkoxylated alkylamine which is component (B) typically includes some separate polyoxyalkylene glycol. The amount of the separate polyoxyalkylene glycol which is present in component (B) typically does not exceed 30% by weight of the mixture of alkoxylated alkylamine and polyoxyalkylene glycol which is component (B).

The value of each of m and p is preferably at least 5, and especially is at least 8. In general each of m and p does not exceed 80, and is especially not more than 50. It will be appreciated that m and p are average figures and, as in most polymeric materials, the values of m and p are different in the molecules which together form the material which is component (B). The values of m and p are generally similar but not identical. We have obtained a useful result when the group A is ethylene and m and p together total about 20.

Component (C) of the composition is a polyoxyalkylene alkyl or alkylaryl ether phosphoric acid ester. It is preferred that component (C) contains a high proportion (at least 60% by weight) of monoester. Component (C) is typically a compound of the general formula:

$$R^4-O-(AO)_q-\underset{\underset{OR^6}{|}}{\overset{\overset{O}{\|}}{P}}-OR^5$$

where
A is as defined for component (B);
$R^4$ is an alkyl or alkylaryl group;
$R^5$ and $R^6$, which may be the same or different, are hydrogen or a group $R^4-O-(AO)_q-$; and
q is a number which has a value of at least one and not more than 50.

Component (C) is typically a mixture of mono-, di- and tri-esters. Component (C) is preferably a mixture of which the major portion by weight is a component in which both $R^5$ and $R^6$ are hydrogen. When $R^5$ and/or $R^6$ is a group $R^4$—O—(AO)$_q$—, the group $R^4$ is generally the same in all of the groups $R^4$—O—(AO)$_q$—but the value of q is typically different in each of the groups $R^4$—O—(AO)$_q$. When $R^5$ and/or $R^6$ are other than hydrogen, component (C) is, or contains, di- or tri-esters. It is preferred that these di- and tri-esters do not exceed 40% by weight of component (C).

The group $R^4$ is preferably a higher alkyl group, as herein defined. It is especially preferred that $R^4$ is an alkylaryl group in which the alkyl portion contains at least about 4 carbon atoms and particularly at least 6 carbon atoms, for example as in an octyl, nonyl, decyl, dodecyl, tridecyl, tetradecyl, hexadecyl or octadecyl group. In general when $R^4$ is an alkylaryl group, the alkyl group does not contain more than 30 carbon atoms, particularly not more than 24 carbon atoms.

The polyoxyalkylene phosphoric acid ester is typically prepared by an alkoxylation process which results in a product which contains separate polyoxyalkylene glycol. The amount of this separate polyoxyalkylene glycol typically does not exceed 30% by weight of the mixture of polyoxyalkylene phosphoric acid ester and polyoxyalkylene glycol which is component (C), and may be less than 15% by weight and especially not more than 5% by weight of the mixture.

The value of each q is preferably at least 2 and especially is at least 5. In general q does not exceed 40 and is especially not more than 20. It will be appreciated that q is an average value and that component (C) will be a mixture of compounds in each of which the value of q is different. We have obtained a useful result when component (C) is predominantly (at least 60% by weight) a monoester in which $R^4$ is a p-nonylphenyl group, $R^5$ and $R^6$ are both hydrogen, A is an ethylene link and q has a value of about 9.

Component (D) is a glycol, preferably one containing not more than 5 carbon atoms. Suitable glycols include ethylene glycol, diethylene glycol, triethylene glycol and propylene glycol. Particularly preferred glycols are ethylene glycol and, especially, propylene glycol.

The composition of the present invention can consist of components (A), (B), (C) and (D) only, where (B) and (C) may include separate polyoxyalkylene glycols. However, such compositions have a high viscosity which may exceed 1000 mPa.s. As is discussed hereafter, the compositions of the present invention can be used as compatibility agents for mixtures which are to be sprayed and hence it is preferred that the composition has a lower viscosity than 1000 mPa.s. We have found that compositions which additionally include water in an amount by weight which is at least equal to the weight of the glycol which is component (D) have a lower viscosity than a corresponding composition which does not contain water. Hence, especially preferred compositions in accordance with the present invention contain components (A), (B), (C) and (D) together with water.

One composition in accordance with the present invention consists essentially of (A) 15 to 35% by weight of an alkyl glucoside of the general formula $C_nH_{(2n+1)}O(C_6H_{10}O_5)_bH$, where n has an average value of 9; and b has an average value of greater than one and not more than two;

(B) 15 to 40% by weight of an ethoxylated alkylamine obtained by ethoxylation of a primary amine and having about 20 oxyethylene repeat units and a mixture of alkyl groups containing 13 to 15 carbon atoms and containing 0% up to 30% by weight of polyoxyethylene glycol;

(C) 15 to 28% by weight of a polyoxyethylene p-nonylphenyl phosphoric acid ester mixture containing at least 60% by weight of the monoester having about 9 oxyethylene repeat units and also containing 0% up to 30% by weight of polyoxyethylene glycol; and (D) 5 to 20% by weight of ethylene glycol or propylene glycol, where the total weight of (A), (B), (C) and (D) aggregates to 100% and which contains water in an amount of 0 to 40% by weight relative to the weight of (A), (B), (C), (D) and water.

A composition of the foregoing type containing 10% by weight of water is a clear amber coloured liquid having a viscosity of about 1200 mPa.s. This liquid has a high flash point, it remains clear and liquid at a temperature of −5° C. and the properties of the liquid do not change after being stored for one week at 40° C.

A particularly useful composition in accordance with the present invention consists essentially of (A) 15 to 35% by weight of an alkyl glucoside of the general formula $C_nH_{(2n+1)}O(C_6H_{10}O_5)_bH$, where n has an average value of 9; and b has an average value of greater than one and not more than two;

(B) 15 to 40% by weight of an ethoxylated alkylamine obtained by ethoxylation of a primary amine and having about 20 oxyethylene repeat units and a mixture of alkyl groups containing 13 to 15 carbon atoms and containing 0% up to 30% by weight of polyoxyethylene glycol;

(C) 15 to 28% by weight of a polyoxyethylene p-nonylphenyl phosphoric acid ester mixture containing at least 60% by weight of the monoester having about 9 oxyethylene repeat units and also containing 0% up to 30% by weight of polyoxyethylene glycol; and (D) 5 to 20% by weight of propylene glycol; and 5 to 40% by weight of water relative to the weight of (A), (B), (C), (D) and water wherein the weight of propylene glycol is less than the weight of water.

A composition of the foregoing type containing about 23% by weight of water, is a clear amber coloured liquid having a viscosity of about 350 mPa.s. This liquid has a high flash point, it remains clear and liquid at a temperature of −5° C. and the properties of the liquid do not change after being stored for one week at 40° C.

A characteristic of compositions in accordance with the present invention, particularly the foregoing specified compositions, is that such compositions are readily soluble in liquid fertilisers.

The compositions of the present invention are readily prepared by mixing together components (A), (B), (C) and (D). Mixing to obtain compositions including water is conveniently effected by first mixing water and the glycol, adding the glycoside, which may be added as an aqueous solution, and mixing until the glycoside is dissolved, adding the polyoxyalkylene phosphoric acid ester with stirring and then adding the alkoxylated alkylamine and mixing with moderate stirring for example by hand or using a stirrer at a rate up to about 100 r.p.m. If the glycoside is added as a solid glycoside, mixing in with the water/glycol mixture is effected with heating, typically at a temperature of 50° to 60° C., and mixing is continued until the glycoside is completely dissolved in the water/glycol mixture.

The compositions of the present invention can be used as compatibility agents for mixtures of a liquid fertiliser and a toxicant. The compositions may also be used as compatibility agents for toxicants, some or all of which may be used as the active ingredient in a pesticide.

The liquid fertiliser can be any commercially available liquid fertiliser and may be a slurry or a solution. The liquid fertiliser may be used as supplied or diluted with water. The fertiliser may be, for example a liquid nitrogen fertiliser containing 30% by weight of nitrogen (referred to commercially as 30-0-0), a mixed nitrogen-phosphorus fertiliser of composition 10–34% by weight (referred to commercially as 10-34-0) or a nitrogen-phosphorus-potassium containing liquid fertiliser of composition 12-4-6% by weight (referred to commercially as 12-4-6). We have found, when using nitrogen-phosphorus-potassium containing liquid fertilisers, the preferred composition required to achieve compatibility varies with the nitrogen content of the liquid fertiliser and at a low nitrogen content, that is less than about 10% by weight of nitrogen, the composition preferably contains a lower proportion of the alkoxylated alkylamine and a higher proportion of water. More specifically, if the liquid fertiliser contains less than 10% by weight of nitrogen, the preferred composition contains water in an amount, by weight, which is at least equal to that of the alkoxylated amine and typically the weight ratio of water to alkoxylated amine is 60:40 or 70:30.

The toxicants which are used include the active ingredients of herbicides, insecticides and fungicides and mixtures thereof. The toxicants may be used alone but are typically used as the active ingredient of a pesticide formulation. A wide range of commercially available toxicants may be used together with a liquid fertiliser and compatibility agent in accordance with the present invention to produce a compatible mixture of fertiliser and toxicant.

Toxicants which may be used in compatible mixtures in accordance with the present invention and which can be used as the active ingredient in a herbicide formulation include 6-chloro-N-ethyl-N'-isopropyl-1,3,5-triazinediyl-2,4-diamine (atrazine); 3-(3-chloro-p-tolyl)-1,1-dimethylurea (chlortoluron); 2-chloro-2',6'-diethyl-N-methoxymethylacetanilide (alachlor); S-2,3,3-trichloroallyl-di-isopropyl-(thiocarbamate) (tri-allate); N-(1-ethylpropyl)-2,6-dinitro-3,4-xylidine (pendimethalin); 1,2-dimethyl-3,5-diphenylpyrazolium ion (difenzoquat); butyl-(RS)-2-[4-(5-trifluoromethyl-2-pyridyloxy)-phenoxy]propionate (fluazifop-butyl); a mixture of 1:4 by weight of (2,4-dichlorophenoxy)acetic acid (2,4D) and (±)-2-(4-chloro-2-methylphenoxy) propionic acid (mecoprop) and alpha, alpha, alpha-trifluoro-2,6-dinitro-N,N-dipropyl-p-toluidine (trifluralin). A toxicant which may be used in compatible mixtures in accordance with the present invention and which can be used as the active ingredient in an insecticide formulation is 1,2,3,4,5,6-hexachlorocyclohexane (mixed isomers) (HCH or BHC). The foregoing are given by way of example only and the skilled worker will be aware of many other toxicants which can be used as the active ingredient of a pesticide formulation. Such other toxicants may be used as a component of a compatible mixture in accordance with the present invention. For convenience hereafter the toxicants will be referred to by the common name thereof which is given in brackets in the foregoing listing.

We have found that the composition of the present invention is at least as effective as commercially available compatibility agents and for many mixtures tested the composition of the present invention has been found to be effective in obtaining a compatible system at a lower level than the commercially available materials. In many systems tested, less than 0.25% by weight of the composition of the present invention produced a compatible system. Preferred amounts of the composition of the present invention are in the range from 0.01 to 0.2% by weight, especially 0.05 to 0.15% by weight, the proportions being w/v based on the liquid fertiliser.

Compatible systems in accordance with the present invention can be prepared by any suitable mixing method but it should be appreciated that the most suitable technique will be dependent on the particular materials being mixed together. The composition of the present invention is prepared first and thereafter the preformed composition is mixed with the liquid fertiliser and one or more toxicants.

The most suitable mixing technique is to first mix together the compatibility agent and the liquid fertiliser. If the toxicant is a wettable powder (W.P.) or suspension concentration (S.C.) formulation, or water dispersible granules, it is first mixed with an equivalent weight of water and then added to the fertiliser/compatibility agent mixture, which may be, for example, in a spray tank. An emulsifiable concentrate formulation, or a toxicant solution can be added to the fertiliser/compatibility agent mixture without being premixed with water or other solvent. If a mixture of toxicants is being mixed with the liquid fertiliser, a wettable powder or suspension concentrate formulation is added first, after being premixed with water, an emulsifiable concentrate formulation is then added and finally an aqueous solution of water soluble toxicants. However, we have found that other methods may be more effective with certain mixtures, for example to blend an emulsifiable concentrate formulation with a N/P liquid fertiliser, for example a 10-34-0 liquid fertiliser, mixing is more readily effected by adding the composition of the present invention to the toxicant, that is the emulsifiable concentrate formulation, rather than to the fertiliser solution, and then adding the mixture of emulsifiable concentrate formulation plus composition to the fertiliser solution.

The mixture is agitated to obtain a compatible blend but once agitation has ceased no separation or flocculation should occur within 30 minutes, preferably for at least one hour and especially for at least two hours.

The mixture of liquid fertiliser and toxicant is typically sprayed onto the ground from a spray tank and, to reduce the risk of separation, the contents of the spray tank may be agitated during spraying. Alternatively, if the mixture is allowed to stand before being used or between two spraying operations, it is desirable to agitate the mixture before spraying. It is generally preferred to prepare the mixture of liquid fertiliser and toxicant a short time, typically less than one hour, before spraying and to spray essentially all of the mixture thus produced.

Various aspects of the present invention are set out in the following illustrative Examples.

EXAMPLE 1

A commercially available ethoxylated phosphoric acid ester was mixed with ethylene glycol in the weight proportions of 70:30 by stirring at ambient temperature. The ethoxylated phosphoric acid ester contained about 70% by weight, of the ester components, of polyoxyethylene(9)-p-nonylphenylphosphoric acid monoester, the remainder being the corresponding di- and tri-esters, together with not more than 5% by weight, relative to the total weight of phosphoric acid ester and glycol, of polyoxyethylene glycol.

To the resulting mixture was then added, whilst continuing to stir, an equal weight proportion of a commercially available glycoside which consisted of 70% by weight of a compound of average formula $C_9H_{19}O(C_6H_{10}H_5)_dH$ where d has an average value of 1.5, the remainder being water.

To the mixture from the previous stage was added, whilst continuing to stir, a commercially available ethoxylated alkylamine in a weight proportion equal to that of the glycoside solution. The ethoxylated alkylamine was a polyoxyethylene(20)-alkyl amine obtained from a primary amine in which the alkyl group is a mixture of alkyl groups containing 13 to 15 carbon atoms.

The resulting product is a clear amber coloured liquid having a viscosity of 1200 mPa.s and a flash point of at least 100° C. The mixture remained clear and liquid after being maintained for one week at −5° C. No change in the properties of the mixture was observed after storing for one week at 40° C.

EXAMPLES 2 to 33

Mixtures of liquid fertiliser and toxicant were prepared using, as a compatibility agent, the composition of Example 1. By way of comparison, mixtures containing one of two commercially available compatibility agents were also prepared.

The compatibility agents were added to the liquid fertiliser in an amount of 0.05, 0.10 and 0.20% w/v relative to the liquid fertiliser. The toxicant was added to the mixture of liquid fertiliser and compatibility agent, with stirring. After adding the toxicant, or toxicants, stirring was continued for one minute and was then stopped. The mixtures were allowed to stand without stirring for two hours and the lowest level of the compatibility agent at which no separation or flocculation occurred was recorded. However, in those cases in which the toxicant was a wettable powder, compatibility was judged by no flocculation after standing for 30 minutes. Details of the fertilisers and toxicants used, and the proportion of compatibility agent required to achieve a compatible system are set out in Table One.

The fertiliser and toxicants were used in proportions as recommended for field spraying at a rate of 200 dm$^3$/ha of fertiliser solution.

TABLE ONE

| | | Compatibility Agent (b) | | |
|---|---|---|---|---|
| Ex | Fertiliser/toxicant (a) | A | B | 1 |
| 2 | N + 3 L | 0.2 | IC | 0.1 |
| 3 | NPK + 3 L | 0.2 | IC | 0.05 |
| 4 | N + 1.5 T + 1.25 L | 0.2 | IC | 0.1 |
| 5 | NPK + 1.5 T + 1.25 L | 0.2 | IC | 0.05 |
| 6 | N + 1* P + 2 L | 0.2 | IC | 0.1 |
| 7 | NPK + 1* P + 2 L | 0.2 | IC | 0.1 |
| 8 | N + 1 G + 2 L | 0.2 | IC | 0.1 |
| 9 | NPK + 1 G + 2 L | 0.1 | IC | 0.05 |
| 10 | N + 1.75 A | 0.2 | IC | 0.1 |
| 11 | NPK + 1.75 A | 0.05 | 0.2 | 0.05 |
| 12 | N + 1.5 T + 1.25 A | 0.2 | IC | 0.1 |
| 13 | NPK + 1.5 T + 1.25 A | 0.1 | IC | 0.05 |
| 14 | N + 1.5 T | 0.1 | IC | 0.05 |
| 15 | NPK + 1.5 T | 0.05 | 0.2 | 0.05 |
| 16 | N + 1.75 S | 0.2 | IC | 0.1 |
| 17 | NPK + 1.75 S | 0.1 | IC | 0.05 |
| 18 | N + 0.75* P + 1.75 S | 0.2 | >0.1 | 0.1 |
| 19 | NPK + 0.75* P + 1.75 S | 0.2 | >0.1 | 0.1 |
| 20 | N + 0.75 G + 1.75 S | 0.2 | >0.1 | 0.1 |
| 21 | NPK + 0.75 G + 1.75 S | 0.1 | >0.1 | 0.05 |
| 22 | N + 1 D + 1.5 S | 0.2 | >0.1 | 0.1 |
| 23 | NPK + 1 D + 1.5 S | 0.05 | >0.1 | 0.05 |
| 24 | N + 1.5 F | >0.1 | IC | 0.1 |
| 25 | NPK + 1.5 F | 0.05 | IC | 0.05 |
| 26 | N + 2 D | 0.05 | IC | 0.05 |
| 27 | NPK + 2 D | 0.1 | IC | 0.1 |
| 28 | N + 1.5 D + 1.5 PS | 0.05 | 0.1 | 0.05 |

TABLE ONE-continued

| | | Compatibility Agent (b) | | |
|---|---|---|---|---|
| Ex | Fertiliser/toxicant (a) | A | B | 1 |
| 29 | NPK + 1.5 D + 1.5 PS | IC | IC | IC |
| 30 | N + 2 PS | 0 | 0 | 0 |
| 31 | NPK + 2 PS | IC | IC | IC |
| 32 | N + 0.75 GC | 0 | 0 | 0 |
| 33 | NPK + 0.75 GC | >0.1 | >0.1 | >0.1 |

Notes to Table One (a)

N is a 30% weight nitrogen liquid fertiliser.

NPK is a 12-4-6% weight nitrogen-phosphorus-potassium liquid fertiliser.

The liquid fertilisers were used in an amount of 100 cm$^3$ in all examples.

L is an emulsifiable concentrate containing 480 g/l of alachlor.

T is an emulsifiable concentrate containing 480 g/l of trifluralin.

P is a wettable powder formulation containing 50% w/v of atrazine.

G is a suspension concentrate containing 500 g/l of atrazine.

A is an emulsifiable concentrate containing 400 g/l of tri-allate.

S is an emulsifiable concentrate containing 330 g/l of pendimethalin.

D is a suspension concentrate containing 500 g/l of chlortoluron.

F is an emulsifiable concentrate containing 250 g/l of fluazifop-butyl.

PS is a solution containing 100 g/l of 2,4-D and 400 g/l of mecoprop.

GC is a suspension concentrate containing 800 g/l of HCH.

The number before the foregoing letters is the volume, in cm$^3$, of the toxicant added to the fertiliser.

* indicates toxicant added as a solid, the quantity in this case being in g.

(b)

A is a commercially available compatibility agent consisting of 70% by weight of nonylphenyl polyoxyethylene(7) phosphoric acid ester, 14.6% by weight of methanol and 15.4% by weight of water.

B is a commercially available compatibility agent consisting of 70% w/w of aqueous sorbitol containing 70% w/w of sorbitol; 15% w/w of an aqueous solution containing 45% w/w of sodium dodecyldiphenyloxide disulphonate; and 15% w/w of an aqueous solution containing 35% w/w of tetrasodium-N-(1,2-dicarboxyethyl)-N-octadecylsulphosuccinamate.

1 is the composition as obtained in Example 1.

The number is the minimum % w/v of A, B or 1 added to the fertiliser to give a compatible fertiliser/toxicant mixture.

> indicates that a compatible mixture was not obtained at the highest level of A, B or 1 which was used.

0 indicates the fertiliser/toxicant mixture was compatible without the inclusion of a compatibility agent IC indicates an incompatible system, compatibility was not achieved at 0.2% w/v of compatibility agent used.

EXAMPLE 34

The procedure of Example 1 was repeated with the following exceptions.

Water and propylene glycol were first mixed together in equal proportions by weight. This mixture was then mixed, in turn, with the aqueous glycoside solution, the ethoxylated phosphoric acid ester and the ethoxylated alkylamine used in Example 1. The percentages by weight of the water, propylene glycol, aqueous glycoside solution, ethoxylated phosphoric acid ester and the ethoxylated amine were 15, 15, 26.25, 17.50 and 26.25.

The resulting product has a viscosity of 350 mPa.s but is otherwise generally similar in properties to the product of Example 1.

EXAMPLES 35 to 37

The procedure of Example 1 was repeated using different ethoxylated alkylamines, as follows:

Example 35—polyoxyethylene(20)-tallow amine.

Example 36—polyoxyethylene(15)-alkyl amine obtained from a primary amine in which the alkyl group is a mixture of alkyl groups containing 13 to 15 carbon atoms.

Example 37—an ethoxylated monoalkyl substituted propane diamine of formula:

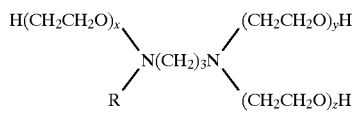

where R is a mixture of alkyl groups Containing 13 to 15 carbon atoms; and x+y+z equals ten.

The procedure of Examples 2 to 33 was repeated using various levels of the mixtures obtained in accordance with Examples 34 to 37. Details of fertilisers and toxicants used and the proportion of compatibility agent required to achieve a compatible system are set out in Table Two.

TABLE TWO

| Fertiliser/toxicant (a) | Compatibility Agent (b) (c) | | | |
|---|---|---|---|---|
| | 34 | 35 | 36 | 37 |
| N + 3 L | 0.15 | >0.1 | 0.1 | 0.2 |
| NPK + 3 L | 0.1 | 0.1 | 0.1 | 0.2 |
| N + 1.5 T + 1.25 L | 0.1 | ND | 0.1 | 0.2 |
| NPK + 1.5 T + 1.25 L | 0.05 | ND | 0.05 | 0.1 |
| N + 1* P + 2 L | 0.15 | ND | >0.1 | 0.2 |
| NPK + 1* P + 2 L | 0.15 | ND | 0.1 | 0.2 |
| N + 1 G + 2 L | 0.15 | ND | 0.1 | 0.2 |
| NPK + 1 G + 2 L | 0.1 | ND | 0.1 | 0.1 |
| N + 1.75 A | 0.1 | ND | 0.1 | 0.1 |
| NPK + 1.75 A | 0.05 | ND | 0.05 | 0.1 |
| N + 1.5 T + 1.25 A | 0.15 | ND | 0.1 | 0.2 |
| NPK + 1.5 T + 1.25 A | 0.1 | ND | 0.05 | 0.1 |
| N + 1.5 T | 0.1 | ND | 0.05 | 0.05 |
| NPK + 1.5 T | 0.05 | ND | 0.05 | 0.05 |
| N + 1.75 S | 0.1 | ND | 0.1 | 0.1 |
| NPK + 1.75 S | 0.05 | ND | 0.05 | 0.1 |
| N + 0.75* P + 1.75 S | 0.15 | ND | 0.1 | 0.2 |
| NPK + 0.75* P + 1.75 S | 0.1 | ND | 0.1 | 0.2 |
| N + 0.75 G + 1.75 S | 0.15 | ND | 0.1 | 0.2 |
| NPK + 0.75 G + 1.75 S | 0.05 | ND | 0.05 | 0.1 |
| N + 1 D + 1.5 S | ND | ND | 0.1 | 0.1 |
| NPK + 1 D + 1.5 S | 0.05 | ND | 0.05 | 0.05 |
| N + 1.5 F | 0.1 | ND | 0.1 | 0.1 |
| NPK + 1.5 F | 0.05 | ND | 0.05 | 0.1 |
| N + 2 D | ND | ND | 0.05 | 0.05 |
| NPK + 2 D | 0.15 | ND | 0.1 | 0.1 |
| N + 1.5 D + 1.5 PS | ND | ND | 0.05 | 0.1 |
| NPK + 1.5 D + 1.5 PS | ND | ND | IC | IC |
| N + 0.75 GC | ND | ND | 0 | 0 |
| NDK + 0.75 GC | ND | ND | >0.2 | >0.1 |

Notes to Table Two (a) and (b) are as defined in Notes to Table One.

(c) 34, 35, 36 and 37 are the compositions of Examples 34, 35, 36 and 37 respectively.

ND is not determined, this compatibility agent was not used with this fertiliser/toxicant mixture.

EXAMPLES 38 to 40

Compositions were prepared as described for Example 34 with the exception that the relative proportions of the alkoxylated alkylamine and the added water were varied whilst keeping the proportions of the propylene glycol, the aqueous glycoside solution and the ethoxylated phosphoric acid ester constant.

Each of the compositions obtained was dissolved in an 8-8-6% weight nitrogen-phosphorus-potassium liquid fertiliser to give a 6% by weight solution of the composition in the liquid fertiliser.

The mixtures were stored for one month at 40° C., 25° C, 5° C. and −5° C. and, after this period of storage, were inspected for compatibility, phase separation or reduced clarity of the mixture indicating incompatibility.

TABLE THREE

| Ex. | A/W (d) | Storage Temperature (e) | | | |
|---|---|---|---|---|---|
| | | 40° C. | 25° C. | 5° C. | −5° C. |
| 38 | 5:5 | IC | C | C | C* |
| 39 | 4:6 | C | C | C | C* |
| 40 | 3:7 | C | C | C | C* |

Notes to Table Three (d) A/W is the ratio, by weight, of the ethoxylated alkylamine to water.

(e) IC means incompatible—separate phases are formed.

C means compatible—a single phase is formed.

* means crystal formation occurs but the liquid clears on warming to 25° C.

We claim:

1. A composition comprising a liquid fertilizer, a toxicant and, as a compatibility agent, a composition which comprises:

(A) 15 to 35% by weight of an alkyl glucoside of the general formula:

$$ROG_n$$

where

R is a $C_8$ to $C_{18}$ alkyl group;

G is a glucoside residue; and a is from 1 to 2.

(B) 15 to 40% by weight of an ethoxylated alkylamine of the general formula:

R¹R²R³N where
R¹ is a $C_9$ to $C_{24}$ alkyl group;
R² is a $C_9$ to $C_{24}$ alkyl group or a group $(AO)_mH$;
R³ is a group $(AO)_pH$;
A is a $C_2$ to $C_5$ alkylene group;
m is 0 or from 1 to 100;
p is 0 or from 1 to 100; and
(m+p) is from 1 to 100,
and containing 0 up to 30% by weight of a polyethylene glycol;
(C) 15 to 28% by weight of a polyoxyalkylene alkyl or alkaryl ether phosphoric acid ester of the general formula:

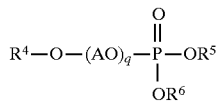

where
A is an alkylene group;
R⁴ an alkyl or alkaryl group;
R⁵ and R⁶, which may the same or different are hydrogen or a group $R^4\!-\!O\!-\!(AO)_q$; and
q is from 1 to 50;
and also containing 0 up to 30% by weight of polyoxyethylene glycol;
(D) 5 to 20% by weight of a glycol selected from ethylene glycol, propylene glycol, diethylene glycol, triethylene glycol and mixtures thereof; and
5 to 40% by weight of water relative to the weight of (A), (B), (C), (D) and water, wherein the weight of glycol is less than the weight of water.

2. A composition as claimed in claim 1 wherein component (A) is an alkyl glucoside of the general formula:

$C_nH_{(2n+1)}O(C_6H_{10}O_5)_bH$ where
n has an average value of 9; and
b has an average value of greater than one and not more than two.

3. A composition comprising a liquid fertilizer, a toxicant and, as a compatibility agent, a composition which consists essentially of:
(A) 15 to 35% by weight of an alkyl glucoside of the general formula:

$C_nH_{(2n+1)}O(C_6H_{10}O_5)_bH$ where
n has an average value of 9; and
b has an average value of greater than one and not more than two;
(B) 15 to 40% by weight of an ethoxylated alkylamine obtained by ethoxylation of a primary amine having about 20 oxyethylene units and a mixture of alkyl groups containing 13 to 15 carbon atoms and containing 0 up to 30% by weight of a polyethylene glycol;
(C) 15 to 28% by weight of a polyoxyethylene p-nonylphenol phosphoric acid ester mixture containing at least 80% by weight of the monoester having about 9 oxyethylene repeat units and also containing 0 up to 30% by weight of polyoxyethylene glycol;
(D) 5 to 20% by weight of propylene glycol; and
5 to 40% by weight of water relative to the weight of (A), (B), (C), (D) and water, wherein the weight of propylene glycol of less than the weight of water.

* * * * *